(12) United States Patent
Schrödl (10) Patent No.: US 8,695,118 B2
(45) Date of Patent: Apr. 15, 2014

(54) METHOD OF REMOVING GLOVES

(76) Inventor: Berthold Schrödl, Vienna (AT)

( * ) Notice: Subject to any disclaimer, the term of this patent is extended or adjusted under 35 U.S.C. 154(b) by 0 days.

(21) Appl. No.: 12/816,627

(22) Filed: Jun. 16, 2010

(65) Prior Publication Data

US 2010/0251458 A1    Oct. 7, 2010

Related U.S. Application Data

(62) Division of application No. 10/576,001, filed as application No. PCT/AT2004/000354 on Oct. 15, 2004, now Pat. No. 7,761,931.

(30) Foreign Application Priority Data

Oct. 16, 2003  (AT) ................. A 1631/2003

(51) Int. Cl.
*A41D 19/00*    (2006.01)
(52) U.S. Cl.
USPC ................................................. 2/161.1
(58) Field of Classification Search
USPC .......................................... 2/161.7, 167, 168
See application file for complete search history.

(56) References Cited

U.S. PATENT DOCUMENTS

| 3,555,564 | A | 1/1971 | Miskell et al. |
| 4,809,365 | A | 3/1989 | Chen et al. |
| 4,876,747 | A | 10/1989 | Coffey et al. |
| 5,020,160 | A | 6/1991 | Cano |
| 5,398,344 | A | 3/1995 | Hirano |
| 5,467,483 | A | 11/1995 | Saadatmanesh et al. |
| 5,579,539 | A | * 12/1996 | Flick ................................. 2/168 |
| 5,768,711 | A | 6/1998 | Wissink |
| 5,864,885 | A | 2/1999 | Grinberg |

FOREIGN PATENT DOCUMENTS

| AT | 6608 | 1/2004 |
| JP | 8-158122 A | 6/1996 |

\* cited by examiner

*Primary Examiner* — Katherine Moran
(74) *Attorney, Agent, or Firm* — Laurence A. Greenberg; Werner H. Stemer; Ralph E. Locher (57) ABSTRACT

A method of removing gloves, such as work gloves, examining gloves or operating gloves having homogeneous bodies with a hand part and a cuff adjacent the hand part. At least one gripping aid is provided on the outer surface of the cuff and at a distance from the rear edge of the cuff. This allows the gloves to be removed in an ergonomic and simple manner without any auxiliary means, even with a very short cuff, without the soiled or contaminated outer side coming into contact with the skin of the person wearing the glove. To this end, at least one gripping aid is arranged in the region of the glove covering the outer region of the wrist, when seen in the peripheral direction of the cuff. Alternatively, at least one gripping aid can extend over at least 180 degrees of the periphery of the cuff, at a distance from the rear edge of the cuff, or each glove in a pair is provided with at least one gripping aid on adjacent peripheral sections of the cuff, said gripping aids being at an angular distance of at least approximately 30 degrees.

8 Claims, 11 Drawing Sheets

METHOD OF REMOVING GLOVES

CROSS-REFERENCE TO RELATED APPLICATION

This is a divisional of U.S. Pat. No. 7,761,931, filed May 11, 2006; which was a National Stage, under 35 U.S.C. §371, of International Application No. PCT/AT2004/000354, filed Oct. 15, 2004; the application also claims the priority, under 35 U.S.C. §119, of Austrian Patent Application A 1631/2003, filed Oct. 16, 2003; the prior applications are herewith incorporated by reference in their entirety.

BACKGROUND OF THE INVENTION

Field of the Invention

The invention relates to a method of removing gloves, especially work, examining, or operating gloves, with a unified glove body, preferably made from liquid-tight, elastic material, such as rubber, and the glove body has a hand part and an adjoining cuff, while at least one gripping aid is provided on the outer surface of the cuff and at a distance from the rear edge of the cuff, and a pair of gloves, consisting of two gloves, especially work, examining, or operating gloves, each with a unified glove body, preferably made from liquid-tight, elastic material, such as rubber, and the glove body has a hand part and an adjoining cuff, while at least one gripping aid is provided on a peripheral section of the outside of the cuff and at a distance from the rear edge of the cuff.

U.S. Pat. No. 4,876,747A describes a glove which can be pulled off by means of a hook, and the gloves of both hands can also be pulled off at the same time from the hands of the user when two hooks are present. For this, an opening or loop is arranged parallel to the edge of the glove and on the hand back side of the cuff into which a hook mounted on the wall or elsewhere can be introduced. Furthermore, this loop can also be grasped by the other hand and the glove pulled off; but then the hook is needed again to pull off the second glove.

A glove of elastomer material is known from U.S. Pat. No. 5,579,539, which has a pull-off aid on the cuff part near the thumb or on the part of the cuff opposite the back hand part, or preferably on the back hand part itself, at a distance from the rear edge of the cuff. Both gloves can be pulled off at the same time with difficulty by an appropriate ergonomically and anatomically awkward twisting of the hands and/or forearms. But due to the necessary twisting of the hands, there is a great risk of the pull-off aid slipping off, in which case the contaminated outer surface of the glove may snap back onto the skin of the wearer.

A pull-off aid is likewise described in U.S. Pat. No. 5,467,483, here in the form of strips, threads, loops, or the like, arranged on the back hand part of the cuff and covered during normal use. However, this pull-off aid hardly allows for a simultaneous pulling off of both gloves. But since one cannot ensure with adequate reliability that the pull-off aid does not become contaminated after opening the cover, the grabbing of the pull-off aid by a hand no longer protected entails the risk of contaminating this hand.

BRIEF SUMMARY OF THE INVENTION

Now, the object of the present invention was to improve a glove of the kind mentioned above so that a pulling off of the gloves is made possible in ergonomic and simple fashion with no aids, even when the cuffs are very short, and without the dirty or contaminated outer side making contact with the skin of the wearer. The pulling on of the gloves should also be facilitated and simplified at the same time, without the wearer having to touch the outside of sterile gloves, for example, with non sterile parts of the body or aids.

A first solution of this problem is characterized in that at least one gripping aid is arranged in the region of the glove covering the outer wristbone region of the wrist, when seen in the peripheral direction of the cuff. For gloves with very short cuffs, this gripping aid could therefore also be arranged on the hand part, in the region of the outer edge of the hand, when seen in the peripheral direction. Thanks to this geometrical arrangement of the gripping aid which can be used as a gripping aid, the gripping aid of each glove can be grasped by the other respective hand in a favorable position of the arms and hands held diametrically opposite and parallel to each other and used to pull off the glove. Thus, the dirty or contaminated outside of the gloves does not have any skin contact, but is only touched with the hand protected by the other glove.

Advantageously, the at least one gripping aid extends for an angular region of around 90°, starting at a peripheral part of the cuff that covers the outer wristbone region of the wrist. The term wristbone region defines primarily the position in the peripheral direction on the cuff, since this will lie closer to the rear end of the cuff than the hand part of the glove for an easier grasping of the gripping aid.

According to another advantageous embodiment, at least one gripping aid starts at a peripheral part of the cuff, covering the outer wristbone region of the wrist, and extends for an angular region of around 90° onto the peripheral part of the cuff covering the inner surface of the hand.

A second solution for the above-stated problem can be achieved by the features that at least one gripping aid extends across at least 180° of the periphery of the cuff at a distance from the rear edge of the cuff. Thanks to this variant of the gripping aid which can be used as a gripping aid, the glove can be grasped by the other respective hand in any position of the arms and hands that is comfortable to the wearer, held diametrically opposite and parallel to each other, and pulled off from the hand, while any dirty or contaminated outer side of the gloves will not have any contact with skin, but instead will only be touched with the hand protected by the other glove.

Advantageously, the at least one gripping aid extends across the entire periphery of the cuff. This maintains the greatest possible freedom in the relative position of the hands and forearms of the wearer during the pulling off process.

According to another embodiment of this solution, the gripping aid can be interrupted once or several times, which facilitates the secure grasping of the gripping aid even when the surface is moist, for example.

A third solution version for the above stated problem is given according to the invention by a pair of gloves which is characterized in that at least one gripping aid is provided on each glove of the pair of gloves, and the gripping aids are provided at adjoining peripheral sections of the cuff on both gloves and have an angular spacing of at least around 30°. This angular spacing pertains to the geometrical center of the gripping aid, whereas the interval free of gripping aids between two gripping aids can subtend a smaller angular interval, especially when the gripping aids are very extensive. Thanks to this geometrical arrangement of the gripping aid, the gripping aid of each glove can be easily grasped in the natural position of the arms and hands of the other hand, held diametrically opposite and in parallel, and used to pull off the glove. Any dirty or contaminated outer side of the gloves will make no contact with the skin, but instead it will only be touched with the hand protected by the other glove. The gloves when pulled off preferably at the same time and diametrically opposite each other will be automatically turned inside out at the same time, making their subsequent handling simpler and safer.

Advantageously, according to one embodiment of the invention, the gripping aids on both gloves have an angular spacing of at least around 135°, and preferably the gripping aids on the two gloves are arranged essentially diametrically opposite each other. These values for the angular spacing of the gripping aids ensure the ergonomically most favorable pull-off procedure for the overwhelming majority of glove wearers, and also the best protection against unintentional contamination of the skin.

According to another embodiment of the inventive pair of gloves, for easier and more secure grasping at least one gripping aid extends across an angular region of at least around 90°.

An embodiment with especially many and diverse uses, allowing the greatest freedom for the relative twisting of the hands and forearms of the glove wearer, is characterized by the additional feature that at least one gripping aid extends across the entire periphery of the cuff.

It could also be provided that the gripping aid is interrupted once or several times, which can in most cases improve the grasping and holding of the gripping aid.

In order to facilitate the pulling on, as well as the pulling off when the cuff is already turned over once and also prevent the skin of the wearer being touched by a still contaminated glove in the further pulling off procedure, according to another embodiment of the invention at least one gripping aid can additionally be provided on the inner surface of the cuff. The term "inner surface" in this regard denotes the side of the cuff facing the skin of the wearer during the ordinary wearing of the gloves.

Advantageously, at least one gripping aid lies closer to the hand part on the inside of the cuff, than a gripping aid on the outside of the cuff.

An especially ergonomically favorable pulling off process for the simultaneous removal of both gloves is made possible by one embodiment of the invention in which one gripping aid lies closer to the hand part of the glove on the outside of the cuff, covering the outer wristbone region of the wrist, than a gripping aid on a peripheral section of the cuff covering the inner surface of the hand.

A preferred embodiment of the invention provides for at least one gripping aid having at least one continuous opening. This type of gripping aid allows one or more fingers of the other hand or even a rod- or hook-shaped aid to be slipped into or through the gripping aid, thereby providing good protection against slipping off from or out of the gripping aid.

Preferably, a gripping aid is fashioned as a loop raised up from the cuff. This type of gripping aid also includes variants with a tongue lying flat against the cuff during normal use of the glove.

Another advantageous variant provides for at least one gripping aid having a pocket open on at least one side. Such pockets also enable a secure grasping by slipping in, for example, one or more fingers of the other hand, or a helping implement.

In order to facilitate slipping one or more fingers of the other hand into the tongue or pocket, or provide an ergonomically favorable position for this, according to another feature of the invention the orientation of at least one gripping aid can deviate by no more than 80° from the lengthwise axis of the cuff, preferably it can essentially coincide with the lengthwise axis of the cuff.

On the other hand, however, at least one gripping aid could be oriented essentially transverse to the lengthwise axis of the cuff.

The grasping and also the secure holding when manipulating the glove during the pull-off, as well as the pull-on process, can also be facilitated for many types of gripping aids in that at least one gripping aid is provided on an intermediate part or produced as a single piece with it, and the intermediate part itself is arranged on the cuff or produced as a single piece with it.

As an alternative to the above-mentioned configurations of gripping aids, according to another embodiment of the invention at least one gripping aid can be fashioned as a flap-, tongue-, or threadlike appendage. At the end or in the length of such gripping aids, especially those of flap- or tongue-shape, openings, indentations, or the like can also be provided, which allow one to slip one or more fingers of the other hand or a helping implement into and through them.

Another alternative embodiment of the invention is characterized in that at least one gripping aid is fashioned as a hollow bulge of the glove, open toward the inside of the glove. In this way, when the glove is placed on the hand, its material is arched upward or forms a fold, which can then be easily grasped by the other hand, as opposed to when the material is lying flat. This gripping aid can be fashioned essentially in circular symmetry, or also oblong, and with a preferential direction in either case.

Advantageously, according to another embodiment of the invention, at least two gripping aids can be provided adjoining each other in the peripheral direction of the cuff, with different orientation to the lengthwise axis of the cuff.

When there is a single oblong gripping-aid, the same effect is achieved by providing that at least one gripping aid changes its orientation to the lengthwise axis of the cuff at least once.

Advantageously, at least one gripping aid can be provided with surface structures which enhance the grip. This can be done by appropriate roughening of the material of the cuff surface, or by various surface structures such as knobs, ribs, or the like. Many different shapes of these surface structures are also possible, such as hemispherical, essentially conical or even pyramidal knobs.

For both centrally symmetrical and oblong gripping aids, the grabbing can be improved in that at least one gripping aid has a cross section becoming at least partially larger from the surface of the cuff. The gripping aid in such a configuration is, for example, similar in cross section to the Greek letter omega, or resembles a cone placed on its head, or a triangle placed on its tip in cross section.

The first stage of the pulling off of the glove is substantially facilitated according to one advantageous embodiment of the invention by providing a stretch region in the area of at least one gripping aid.

When the gripping aids are manufactured separately and then joined to the cuff of the glove, there also exists the possibility of improving the grip of the gripping aid in that at least one gripping aid is made from a different material than the cuff of the glove, preferably one with a better grip.

As an alternative or also in addition to a series of gripping aids in the peripheral direction—or also in the lengthwise direction of the glove arrangements characterized in that at least two gripping aids with different orientation to the lengthwise axis of the cuff are adjacent to each other and/or overlap each other in the peripheral direction of the cuff can also be advantageous.

The strength of the glove and thus its resistance to damage and accidental contamination of the skin of the wearer through ripped areas of the glove can be improved in that the gripping aid and/or at least the transition region between cuff and gripping aid is reinforced, for example, by means of interstitial reinforcement fibers.

The following description will explain the invention in more detail by means of the enclosed drawings of exemplary embodiments of the inventive gloves or pairs of gloves.

DESCRIPTION OF THE INVENTION

Figure 1:
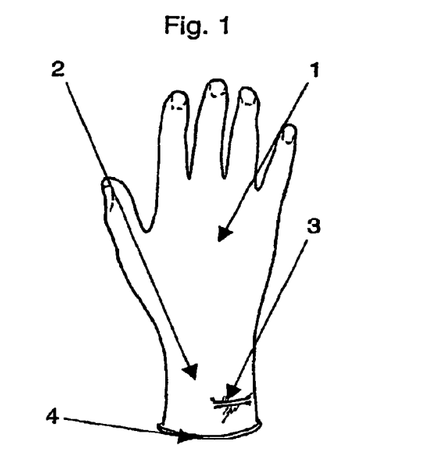
FIG. 1 shows a glove in the most simple configuration of the invention with a single looplike gripping aid.

FIG. 1 shows in top view from above a right glove, consisting of a unified glove body H, while the glove body has a hand part 1 and a cuff 2 adjacent to the latter. The inventive configuration of the glove H is used primarily in variants lying tightly and directly against the hand of the wearer, preferably made from liquid-tight, elastic material, such as rubber, serving preferably as examining or operating gloves. Nevertheless, the benefits of the inventive glove design also extend to all other kinds of gloves, such as fabric or leather gloves or even all kinds of disposable gloves made of plastic, as are customary in supermarkets and gas stations.

Figure 2:
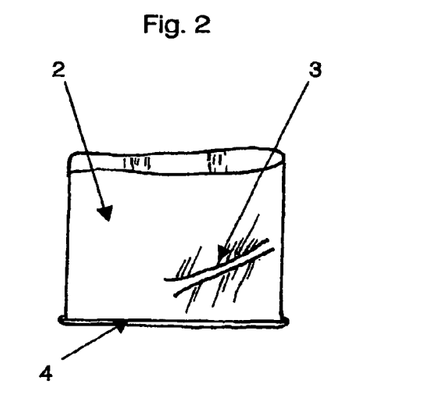
FIG. 2 is a view of the cuff region of an inventive glove, again with looplike gripping aid on enlarged scale.

Now, on a peripheral segment on the outside of the cuff 2 there is provided, for example, a looplike gripping aid 3a. This at least one gripping aid 3a is provided on a peripheral part of the cuff 2, which covers the wristbone region of the hand on the outside, although this statement must be considered merely an approximate positioning in the peripheral direction. The gripping aid 3a can also extend across a certain angular region in the peripheral wristbone region. Looking in the lengthwise direction, the gripping aid 3a can be situated in very different positions, and for gloves with very short cuffs 2 it can even be moved to the region of the actual hand part 1 and lie in the region of the wrist or even the edge of the hand. These gripping aids and all others yet to be explained are advantageously so little removed from the glove body H or stand out so little from it that they can be easily and firmly grasped, on the one hand, but in no way impede the work or examination procedures, etc. They are also so far away from the rear edge 5 of the cuff 2 that there is no danger of touching with one glove-protected hand the tissue (skin) of the opposite hand when putting on or taking off the gloves FIG. 2 shows the gripping aid 3a in larger scale, it being evident that this gripping aid 3a is made as a single piece with the glove cuff 2 and is raised above the surface of the cuff 2 opposite the skin of the wearer such that one or even several fingers of the other hand or even a helping implement can be inserted for manipulating the glove. This helping implement can be, say, a hook or the like, which can be fixed in place or held by the other hand.

Any type of gripping aid 3a can be provided in any meaningful orientation relative to the lengthwise axis of the cuff 2. FIG. 2 shows a slanting arrangement, for example, of a loop-shaped gripping aid similar to FIG. 1, which optimally allows a pulling force to be exerted from the wristbone region of the glove obliquely across the back side of the hand to the thumb side.

Figure 3:
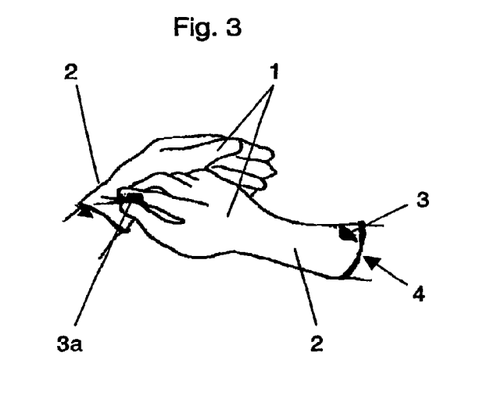
FIGS. 3 to 10 show the diametrically opposite pull-off process with an inventive pair of gloves in perspective view.

FIG. 3 shows the start of the pulling off process of a pair of gloves according to the invention in perspective view. Besides the gripping aid 3a in the wristbone region of the cuff 2 already described in connection with FIG. 1 and FIG. 2, an additional gripping aid 3 is preferably provided on the glove H of the other hand, being provided at a position opposite the back hand part 4, when seen in the peripheral direction, or at a place which is adjacent thereto on at least one side. The first gripping aid, as well as the further gripping aid 3, could also be designed as structures extending for approximately 180°, from the wristbone region to the inner surface of the hand.

Figure 4:
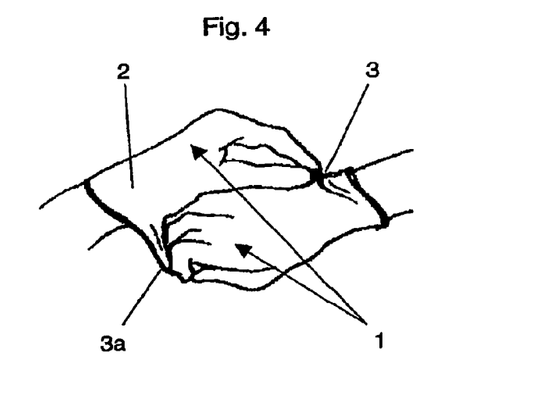
Figure 5:
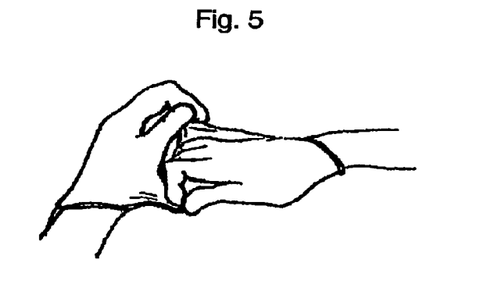
Figure 6:
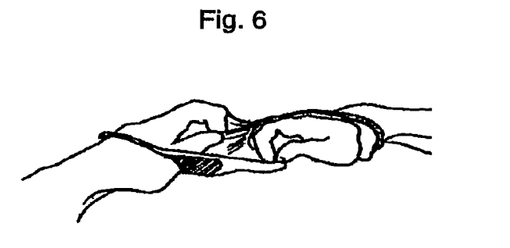
Figure 7:
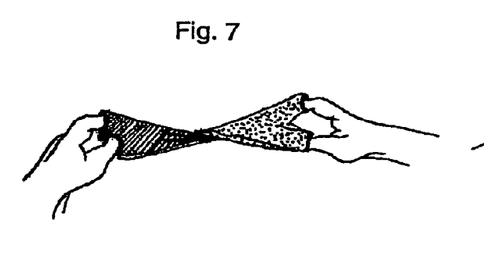
Figure 8:
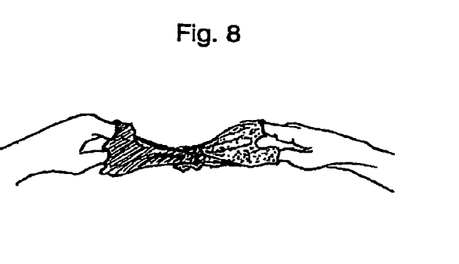
Figure 9:
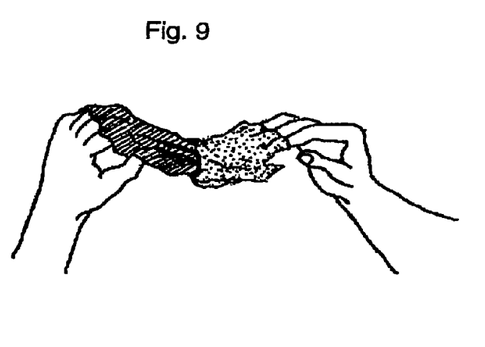
Figure 10:
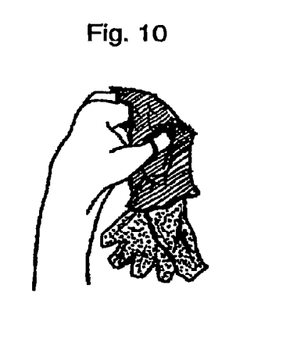

After grasping the gripping aid 3 on the left glove in FIG. 3 with the other, i.e., right hand (FIG. 3), the gripping aid 3a arranged in the wristbone region on the outer side of the second, right glove, as shown in FIG. 4, can be grasped by the left hand in an ergonomically favorable position of both hands and forearms to each other. The skin of the wearer does not make any contact with any dirty or contaminated outer surface of the gloves. As the hands are further moved apart, as can be seen in FIGS. 5 and 6, the gloves will be pulled off diametrically opposite and substantially at the same time from the forearms and then also from the surface of the hand or the back of the hand, and a portion of the gloves with its normally outside situated surface will already be drawn into the other respective glove. As the hands are moved further apart and the gloves are also pulled off from the fingers of both hands, the gloves will finally be fully turned inside out and joined together as they continue to be drawn into each other, as can be seen in FIGS. 7 to 10. Thus, as can be seen in FIG. 10, after pulling off the gloves the user can hold and handle them without coming into contact with their potentially dirty or contaminated outer surface.

Figure 11:
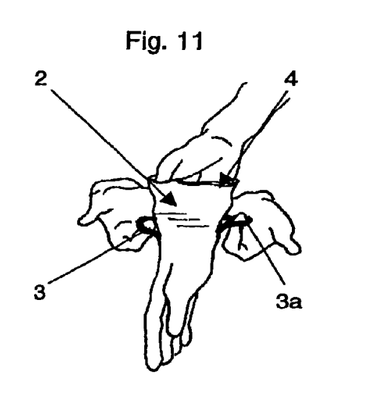
FIG. 11 shows one stage in the putting on of an inventive glove of another embodiment with two gripping aids.

The gripping aid 3, 3a configured and arranged according to the invention not only facilitates the pulling off of the gloves, as explained above, but the user can also more easily slip on the glove by grasping a loop or the like (3, 3a) and slipping on the glove by pulling on it in the direction of the arm or body. The same can be done by a helper, who may already be wearing (sterile) gloves, as shown in FIG. 11, thereby ensuring excellent sterility. Furthermore, this second person can stretch the glove apart by pulling the gripping aids 3, 3a apart, if it has two or more of them, and thereby widening the opening of the glove H. The user of the glove can then slip more easily into the expanded glove opening (and the glove).

Figure 12:
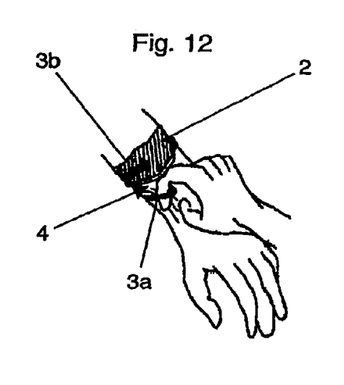
FIG. 12 shows one stage in the putting off of an inventive glove of another embodiment with additional interior gripping aid.

If the cuff 2 of the glove H has already been somewhat turned inside out, or if the exterior gripping aids 3, 3a have been lost or slipped through the fingers, the further pull-off process can also be facilitated by providing at least one gripping aid 3b in addition on the inside of the cuff 2, as shown in FIG. 12. Preferably, such a gripping aid 3b on the inside of the cuff 2 will lie closer to the hand part 1 of the glove H than a gripping aid 3, 3a on the outside of the cuff 2.

Other kinds of gripping aids 3, 3a, 3b, their configurations, arrangements and orientations are then represented as examples, but not limited thereto, in FIGS. 13 to 54.

Figure 13:
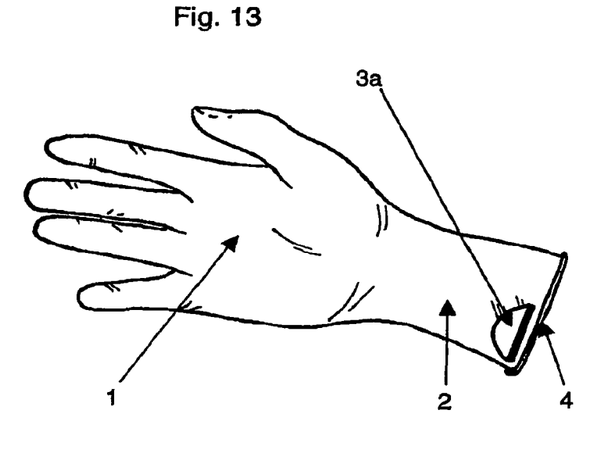
FIG. 13 shows a gripping aid according to another embodiment and in a different position on the cuff.
Figure 14:
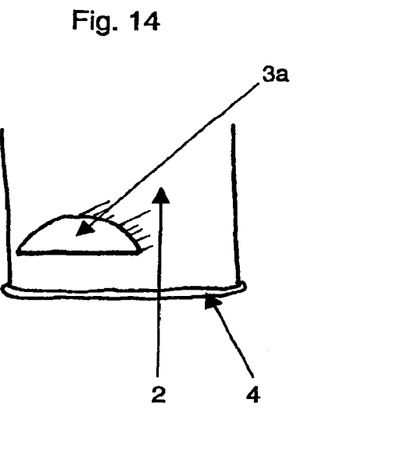
FIG. 14 is a view of the cuff of FIG. 13 in larger scale.

Besides gripping aids 3, 3a in the above described embodiment as a loop with a continuous opening, gripping aids 3, 3a in a tongue or flap configuration can also be provided, as is shown in FIGS. 13 and 14 for a gripping aid 3 arranged on the inside of the hand. This flaplike gripping aid 3 normally lies flat on the surface of the cuff 2, as is also advantageously the case with the looplike and all other configurations of gripping aids 3, 3a, 3b.

Figure 15:
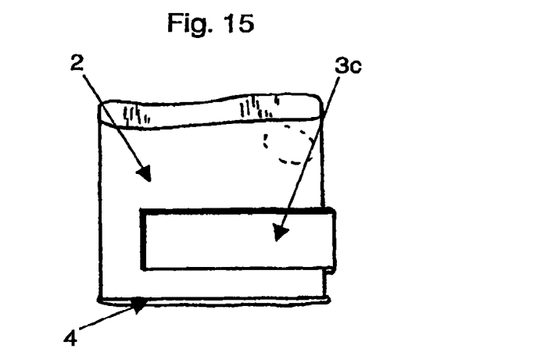
FIG. 15 is a view of a gripping aid extending over a larger periphery.
Figure 16:
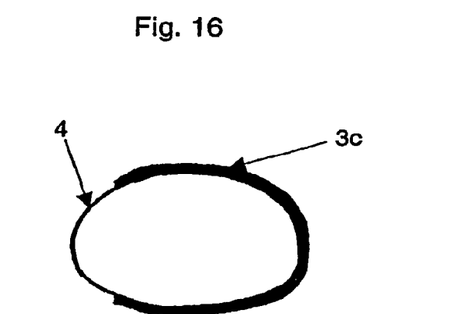
FIG. 16 is a view of the glove of FIG. 15 from the rear.

FIG. 15 shows, in top view, a gripping aid 4 extending across a broad peripheral region, extending around the wristbone region proper onto the side of back of the hand and also the hand's bottom surface of the cuff 2, as is clearly recognizable in the view from behind of FIG. 16. The gripping aid 4 of FIGS. 15 and 16 is also different in construction from the gripping aids 3, 3a, 3b explained thus far, namely, it is designed as a pocket closed off in front, i.e., toward the hand part 1 of the glove H, and open at the rear. Configurations with central ridge and thus a pocket open both in front and at the rear are also possible, into which the fingers of the other hand or also other helping implements can be inserted from the front and/or from behind for pulling the gloves on and off and thus firmly holding the gripping aid.

Figure 17:
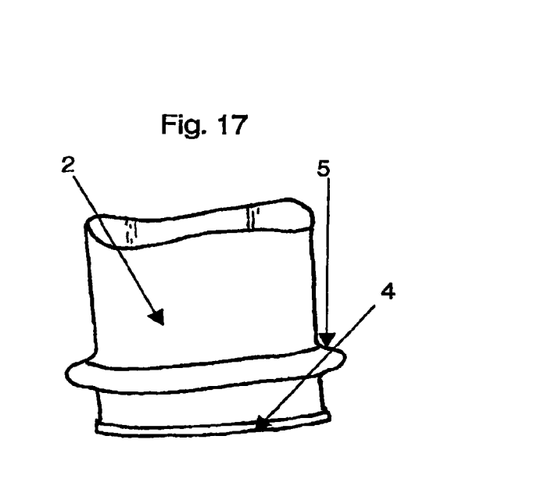
FIG. 17 shows a cuff with gripping aid extending in ridgelike manner across the entire periphery.
Figure 18:
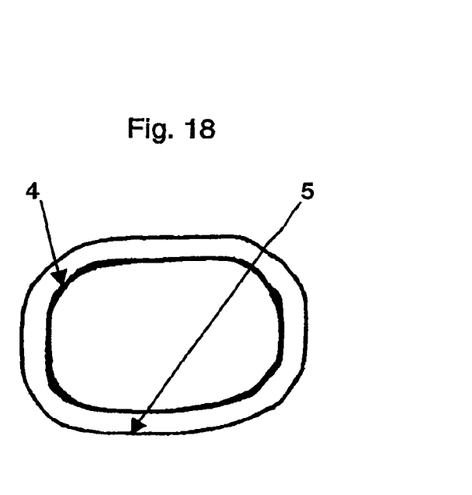
FIG. 18 is a view of the glove of FIG. 17 from the rear.

Another embodiment of the gripping aid is shown in FIGS. 17 and 18, where an elevation 4a running around the entire periphery of the cuff 2 is provided as the gripping aid. This elevation 4a can be formed by a bulge of the material of the cuff 2 itself or by additional material which is applied to the cuff 2. For making the bulge 4a—as for any kind of gripping aids in the form of bulges—the dipping glove mold can be provided with a corresponding projection. This projection after the dipping and finishing of the glove can remain on the dip mold, be removed from the glove, or even be left inside it. The dip mold can also have a permanent bulge.

Of course, gripping aids 4 running around the entire cuff 2 can be provided for pairs of gloves, as well as for individual gloves. These all-around gripping aids 4 could also be in the form of pockets, both with backward pointing opening, i.e., toward the rear edge 5 of the cuff 2, or being open in front, or alternating in both directions.

Figure 19:
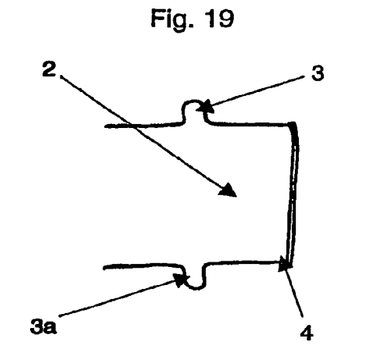
FIG. 19 shows a cuff of an inventive glove in side view, with two gripping aids essentially diametrically opposite to each other.

FIG. 19 shows other gripping aids 4 in bulge configuration, which are designed as essentially circular symmetrical elevations of the cuff 2 and are hollow and open toward the inside of the glove. The latter embodiment can also be provided for the all-around elevation 4a of FIGS. 17 and 18.

Figure 20:
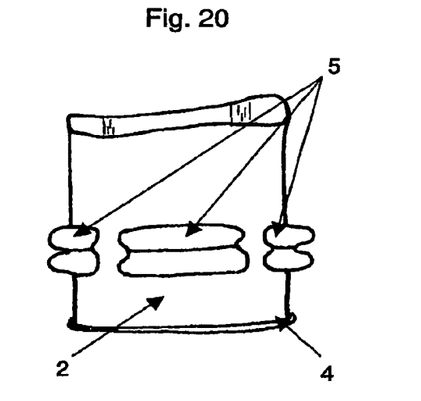
FIG. 20 shows a cuff with inventive gripping aids according to another embodiment along the entire periphery.
Figure 21:
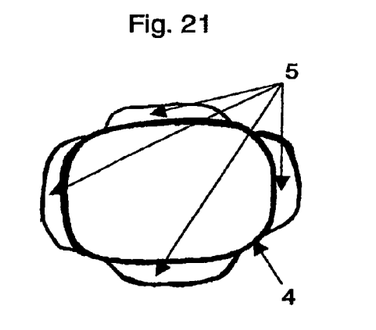
FIG. 21 is a view of the glove of FIG. 20 from the rear.

An embodiment of the gripping aid similar to that of FIGS. 17 and 18 is shown in FIGS. 20 and 21. Two ridges lying close together in the direction of the lengthwise axis of the cuff 2 and being oriented essentially perpendicular to this axis form a gripping aid 4 all around the cuff 2 with the exception of four interruptions. The ridges of the gripping aid 4 extend essentially across an angular region of around 45° and are located—in terms of the periphery—on the side of the back of the hand, the outer wristbone region, the thumb side, and the inner hand surface of the cuff 2.

Figure 22:
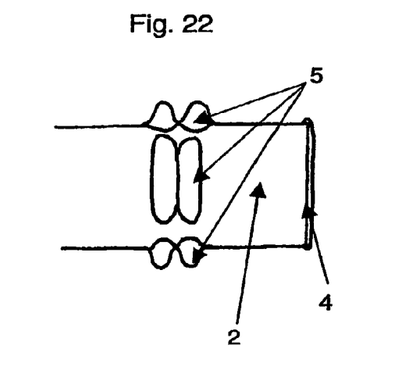
FIG. 22 shows a cuff with gripping aids similar to FIG. 20 in side view.

FIG. 22 shows a cuff with gripping aids 4 similar to FIG. 20 in side view, again designed as two ridges lying next to each other and divided by four interruptions into four separate regions. But whereas FIG. 20 shows an embodiment in which the gripping aid 4 is formed by additional material placed on the cuff 2, the ridges of FIG. 22 are formed by protuberances of the cuff 2 itself, preferably open toward the inside, preferably cavities that are formed during the dipping process in the manufacturing.

Figure 23:
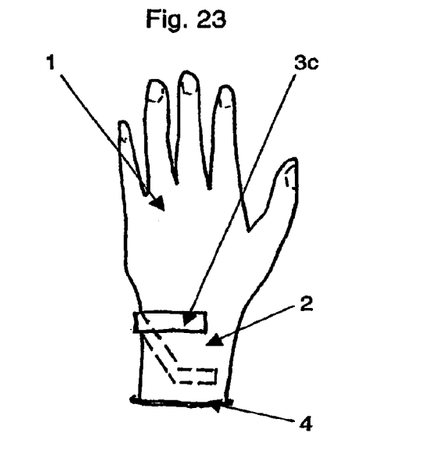
FIG. 23 shows in top view the left glove of an inventive pair of gloves with another embodiment of a gripping aid.

The gripping aid 3 of the left glove of a pair of gloves according to the invention runs on the back hand side of the wristbone region essentially parallel with the rear edge 5 of the cuff, then merges into a segment which runs obliquely in the direction of this rear edge 5 to the inside of the hand, and from there again runs largely parallel to the edge 5 for a short distance.

Figure 24:
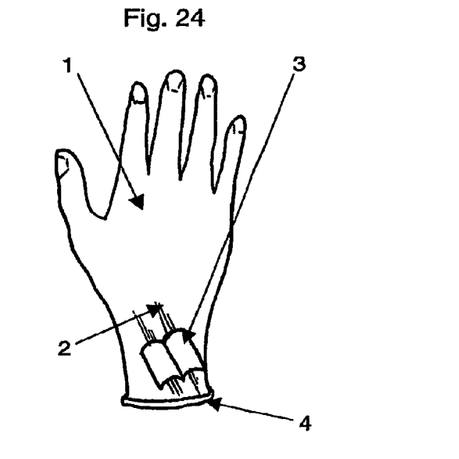
FIG. 24 shows a right glove, with another variant of a gripping aid.

The gripping aid 3a provided in the upper wristbone region of the right glove of a pair of gloves is designed in the shape of two half-tubes, oriented obliquely to the axis of the cuff 2, running in the direction from the wristbone side to the thumb side. The user can slip the fingers of his other hand and/or a helping implement into the half-tube-shaped gripping aid from either side.

Figure 25:
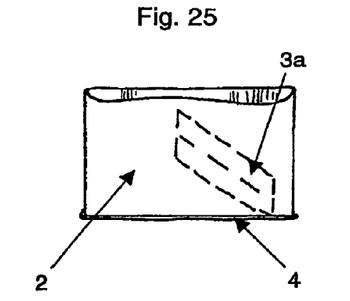
FIG. 25 shows a cuff of a left glove of a pair of gloves in top view with gripping aid designed according to another variant situated at the bottom.

FIG. 25 shows a cuff of a left glove of a pair of gloves as in FIGS. 23 and 24, in top view. An oblong pocket, open in front and in the rear, is applied as a gripping aid 3—indicated by dotted lines—on the hand inner surface of the cuff 2 and peripherally in the thumb region, i.e., the bottom side in FIG. 25. The lengthwise axis of the pocket serving as the gripping aid 3, and in identical fashion its central inner ridge, joined to the cuff 2, is inclined relative to the lengthwise axis of the cuff 2, for example, here it subtends an angle of around 40° with this lengthwise axis of the cuff 2. The gripping aid 3—in each of its configurations—can be arranged at such an angle to the axis of the glove, even clearly deviating from an arrangement oriented normal to the lengthwise axis, that at least one finger of the opposite hand can ergonomically, easily and firmly grasp and hold the gripping aid.

Figure 26:
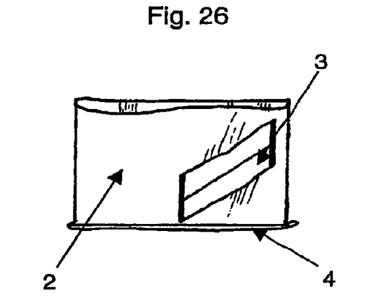
FIG. 26 shows the cuff of the right glove of the pair of gloves with gripping aid arranged on the wristbone side on top.
Figure 27:
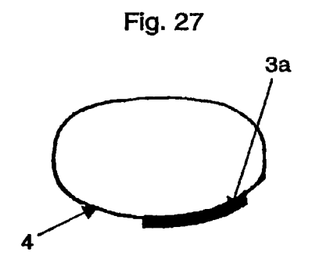
FIGS. 27 and 28 show the cuffs of FIGS. 25 and 26 in a view from behind, FIGS. 29 and 30 each show a top view of cuffs of the left and right glove of a pair of gloves with differently designed gripping aids.
Figure 28:
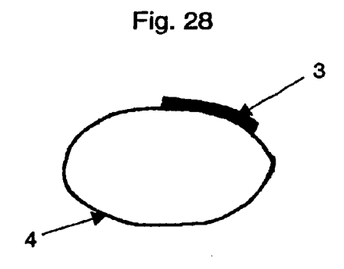

FIG. 26 shows the cuff of the right glove of the pair of gloves with gripping aid 3a arranged at the upper wristbone side, which like the gripping aid 3 of FIG. 25 is designed as a pocket open on both sides. FIGS. 27 and 28 show the cuffs of FIGS. 25 and 26 in a view from behind, revealing the position of the gripping aids on the periphery, as well as their extent along the periphery.

Figure 29:
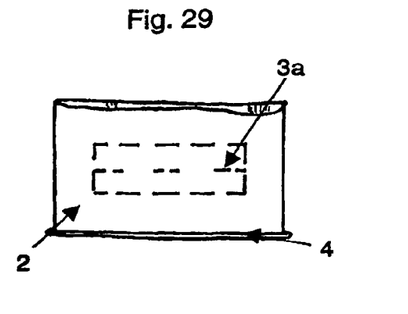
Figure 30:
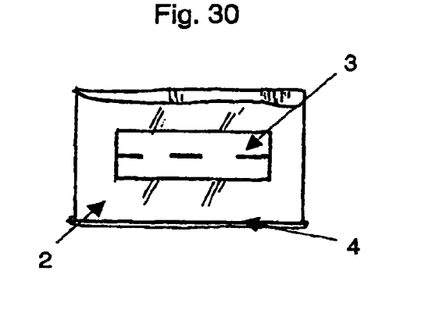
Figure 31:
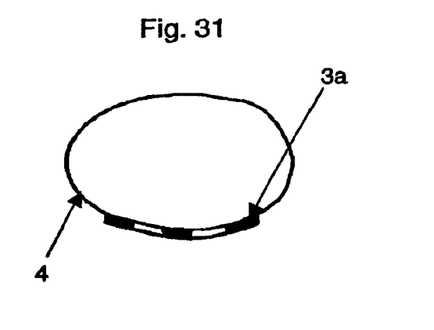
FIGS. 31 and 32 are views of the gloves of FIGS. 29 and 30 from behind.
Figure 32:
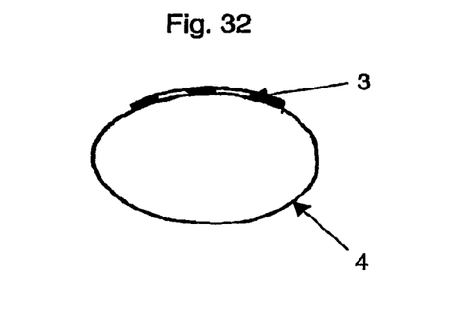

Another embodiment and also arrangement of gripping aids 3 and 3a of a matched pair of gloves—similar to the pairs of FIGS. 23 to 28—are shown by FIGS. 29 and 30. Again, the dotted representation of the gripping aid 3 in FIG. 29 indicates that it is located on the underside of the cuff 2, the inner surface of the hand in terms of periphery, whereas the gripping aid 3a on the opposite glove of FIG. 30 is placed on the back hand side of the cuff 2. The lengthwise axis of the gripping aids 3, 3a are now oriented here exactly perpendicular to the lengthwise axis of the glove and the gripping aids 3, 3a extend across a peripheral angular range of around 90° of the cuff 2. As is especially evident in the views from behind of FIGS. 31 and 32, the gripping aids 3, 3a are formed, for example, by pockets open in front and behind, yet whose central ridge has two interruptions, thus forming two openings through which a finger of the other hand or also a helping implement can be inserted for even better grasping of the gripping aids 3, 3a.

Figure 33:
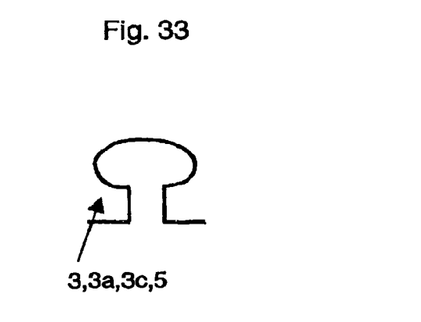
FIGS. 33 to 36 show different kinds of gripping aids in side view.
Figure 34:
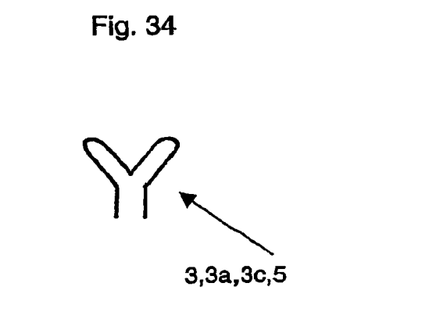
Figure 35:
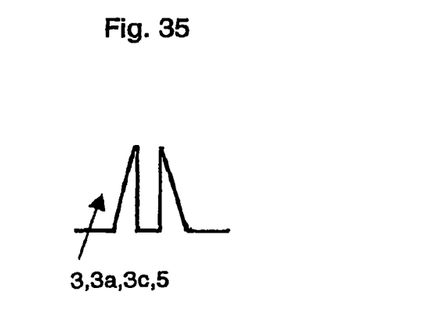
Figure 36:
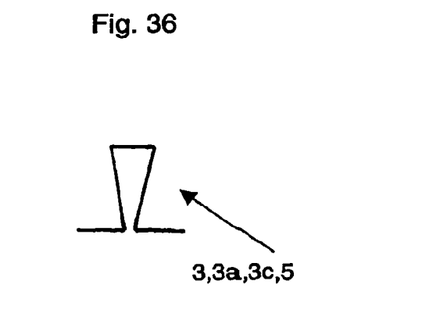
Figure 38:
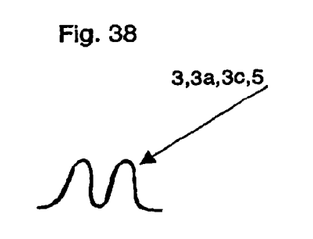
FIG. 38 shows another embodiment of a gripping aid in side view.

Certain cross section shapes can also serve for better grasping of the gripping aids 3, 3a. Thus, FIG. 33 shows a shape of a gripping aid similar to the Greek letter omega, which can also pass into a mushroomlike configuration with outer margin curved downward. A similar upward broadening of the cross section of the gripping aid of FIG. 34, in the shape of the letter "Y", also facilitates the firm holding of the gripping aid. Another variant of the gripping aid is shown in FIG. 35, which corresponds in cross section or side view to two triangles, having one side parallel to and facing each other. A gripping aid cross section in the shape of adjacent, rounded ridges is shown in FIG. 38. Preferable, however, are upwardly broadening shapes, such as gripping aids with the cross section or side view in the form of a triangle placed on its tip, as shown in FIG. 36.

Figure 37:
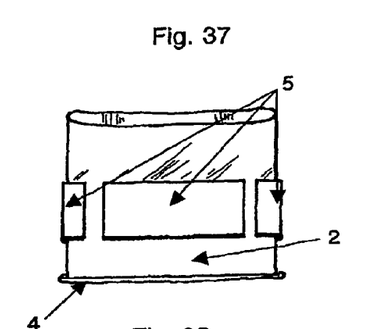
FIG. 37 shows a peripheral, yet interrupted gripping aid in pocket form.
Figure 39:
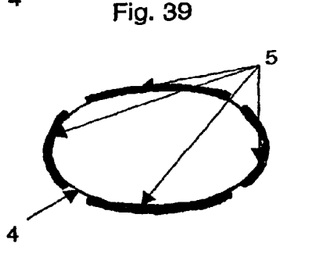
FIG. 39 is a view of the cuff of the glove of FIG. 37 from behind.

For many applications, however, even pockets open in front can be advantageous as gripping aids, such as for the configuration of the inventive glove shown in FIGS. 37 and 39 for example. As made clear by the rear view of the cuff 2 in FIG. 39, a pocket-shaped gripping aid 4 can also run essentially around the entire periphery of the cuff 2 and only be divided into separate regions by small interruptions. The individual pocket-shaped regions extend in terms of angle across somewhat more than 90°, they are positioned at the back of the hand region, the inside of the hand, the wristbone region and the thumb region of the periphery of the cuff 2 and separated from each other by narrow regions of cuff with no gripping aid.

Figure 40:
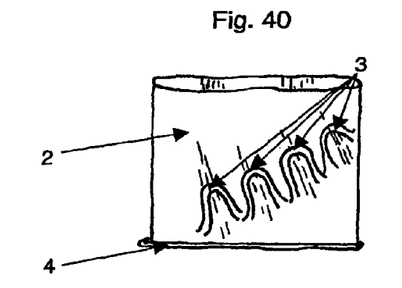
FIG. 40 shows a glove with a series of adjacent gripping aids.

As can be seen in FIG. 40, as many individual gripping aids or gripping aid segments as desired can be provided adjacent to each other, with or without spacing from each other. For example, this is shown in FIG. 40 by means of four individual loops arranged on an oblique line in the upper wristbone region of the cuff 2, each of which is slightly separated from the neighboring loop, and each loop being itself oriented in the direction from the wristbone region to the thumb side of the hand, so as to exert an optimal pulling action in this direction.

Figure 41:
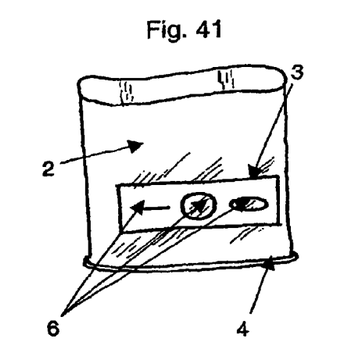
FIG. 41 is a top view of a cuff with yet another embodiment of the gripping aid.

FIG. 41 is a top view of a cuff with yet another embodiment of the gripping aid 3a on the back of the hand side of the cuff 2. A pocket-shaped gripping aid 3a with perpendicular orientation to the lengthwise axis of the glove is additionally provided with openings in the region forming the top side of the pocket. These openings can be, for example, in the form of slots (far left), essentially circular (middle) or elliptical holes (far right), and when the openings have a preferential direction this direction can in principle have any desired orientation relative to the lengthwise axis of the gripping aid 3a and/or the cuff 2 of the glove.

Figure 42:
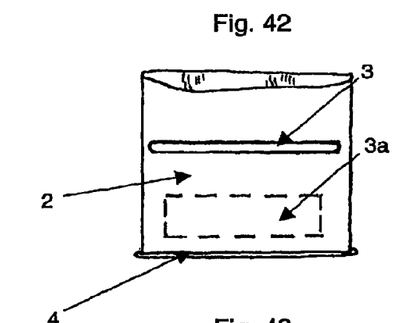
FIG. 42 shows a cuff with two inventive gripping aids in different embodiment and diametrically opposite each other.
Figure 43:
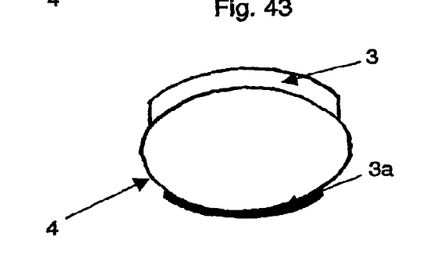
FIG. 43 shows the glove of FIG. 42 in a view from behind.

As shown by another embodiment in FIG. 42, two or more different configurations of gripping aids 3, 3a can also be combined on the same glove, as well as different positions and orientations of the gripping aids relative to each other and/or to the lengthwise axis of the glove. In the example of FIG. 42, a straight, ridgelike elevation oriented perpendicular to the lengthwise axis of the glove is provided on the back of the hand side of the cuff 2 as the gripping aid 3a, and a pocket-shaped gripping aid 3, likewise perpendicular to the lengthwise axis of the cuff 2, is provided diametrically opposite on the inside of the hand. The position in terms of periphery is clearly shown in FIG. 43. Of course, several gripping aids 3, 3a can take up different positions in the lengthwise direction of the glove not only on different gloves, but also on the same glove. Thus, in the exemplary embodiment of FIG. 42, the ridgelike upper gripping aid 3a is further away from the rear edge 5 of the cuff 2 than the pocket-shaped lower gripping aid 3, which is farther from the hand part 1 of the glove. In any case, however, the gripping aid 3, 3a, or 4 lying closest to the rear edge 5 is so far from the rear edge 5 of the cuff 2 that there is no danger of touching the skin or clothing of the wearer, no longer covered by the cuff 2, when grasping the gripping aid 3, 3a, or 4 with a dirty or contaminated glove.

Figure 44:
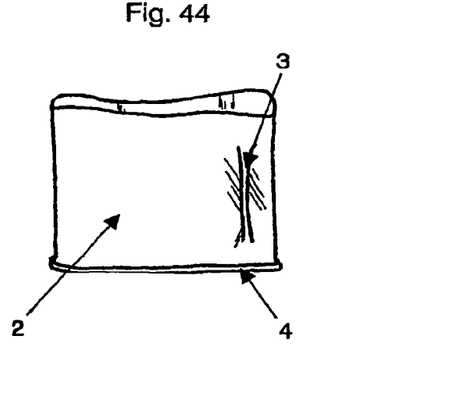
FIG. 44 is a view of a cuff with looplike gripping aid parallel to the lengthwise axis of the cuff.

FIG. 44 is a view of a cuff 2 with loop-shaped gripping aid 3a, oriented parallel to the lengthwise axis of the cuff 2.

Figure 45:
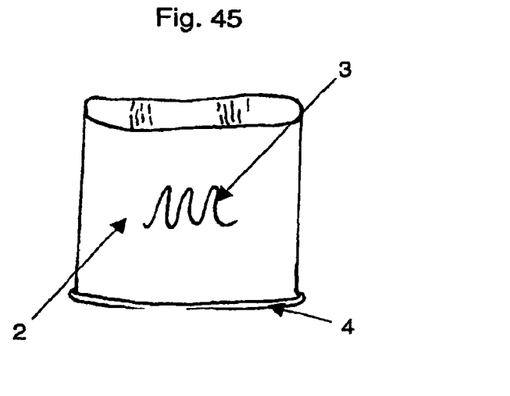
FIG. 45 shows an inventive cuff with threadlike gripping aid.

An entirely different embodiment of a gripping aid 3a is shown by FIG. 45. It is designed as a thread lying against the cuff 2 in serpentine fashion in its state of rest, which can be lifted up from the cuff 2 by the other hand and used to exert a pulling in basically any desired direction.

Figure 46:
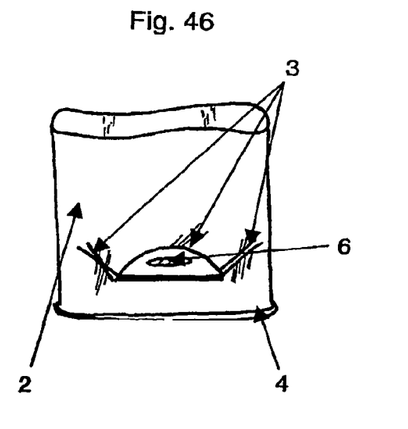
FIG. 46 is a view of a cuff with three consecutive gripping aids of different inventive configuration along the periphery, FIG. 47 likewise shows an inventive cuff with a gripping aid with different orientation in different positions on the periphery.

Several gripping aids, even of different design, can also be directly adjacent to each other, as is shown for example in FIG. 46. Here, on either side of a central loop- or tongue-shaped gripping aid, with a lengthwise hole in addition for secure grabbing, there are arranged looplike gripping aids. The different adjacent gripping aids 3d could be oriented identical or parallel, but they could also have different orientation to each other, as shown. For example, FIG. 46 shows an embodiment in which the outer ends of the outer loop-shaped regions of the gripping aid 3d are shifted toward the hand part 1 of the glove.

Figure 47:
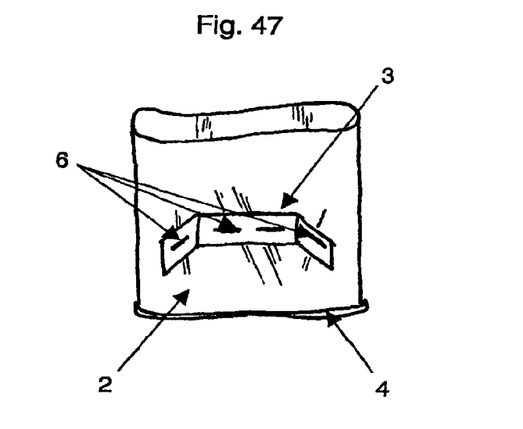

FIG. 47 likewise shows a cuff according to the invention with a gripping aid 3a with different orientation at different positions on the periphery, but the different regions of the gripping aid 3a are configured essentially identical, namely, as a pocket-shaped structure with slits in the upper pocket boundary. But here, in contrast to the gripping aid 3d of FIG. 46, the outer ends of the outer segments of the gripping aid 3a are shifted in the direction of the rear edge 5 of the cuff 2.

To facilitate the grasping and holding of the gripping aids when putting on or pulling off the gloves, various measures can be taken to improve the grip of the surface in the region of the gripping aids. Thus, as shown for example in FIG. 48, grooves can be present, running in the lengthwise direction or the peripheral direction of the cuff 2 when the gripping aids are of oblong shape and also when the gripping aids 4 travel around the periphery. These grooves can also be formed by folding of the material of the cuff 2, which at the same time lets one expand the region of the gripping aid, which can thus be held even more easily and simply.

Figure 48:
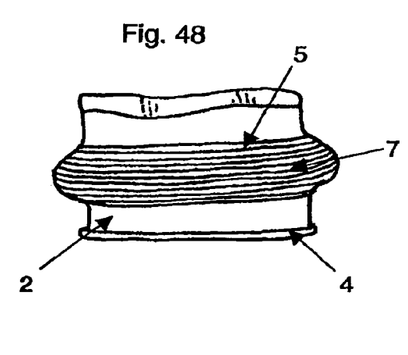
FIG. 48 is the view of a cuff with peripheral gripping aid with surface structure enhancing the grip.
Figure 49:
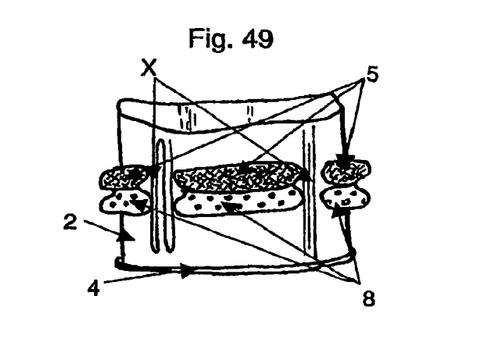
FIG. 49 shows an inventive cuff with gripping aids with surface structures to enhance gripping reliability and with stretch regions between the individual gripping aids.

Besides grooves as in FIG. 48, differently structured surface regions are also possible for the gripping aids. Besides simply roughened surfaces, knobs or other eminences can also be provided over an area. The knobs themselves can have various configurations, such as substantially hemispherical, dowel shaped, conical or pyramidal, and so on. Different configurations can also be provided in adjacent regions, as is shown for example for the peripheral, interrupted gripping aid 4 of FIG. 49. FIG. 49 also reveals that not only the gripping aid itself (as in FIG. 48), but also the intervening regions X can be provided with a stretchable design, such as grooves or folds or stretchable material.

Figure 50:
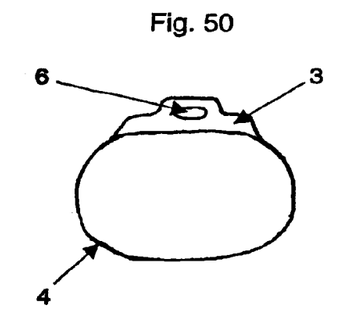
FIG. 50 shows the rear view of a glove with yet another embodiment of a gripping aid.

FIG. 50 shows a gripping aid 3a raised up somewhat above the surface of the cuff 2, here, for example, the back hand side. It consists of a flap-shaped part, whose central region is higher than the side parts and which is also provided with a lengthwise hole oriented transverse to the cuff 2.

Figure 51:
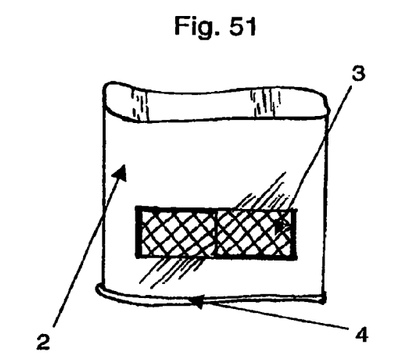
FIG. 51 is a top view of an inventive cuff with different embodiment of the gripping aid.

FIG. 51 shows in top view another embodiment of a cuff 2 according to the invention with a pocket-shaped gripping aid 3a, which on one lengthwise segment is open toward the back, toward the rear edge 5 of the cuff 2, and on the adjoining segment (to the right in the drawing) it is open toward the front, toward the hand part 1 of the glove. In addition, to enhance the grip, the outer surface of the gripping aid 3a is provided with a waffle imprint, for example.

Figure 52:
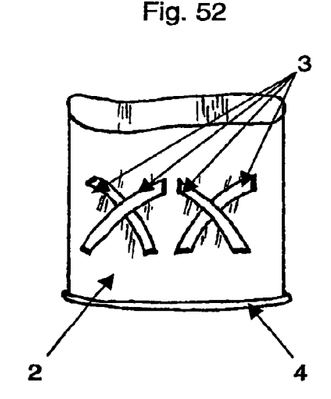
FIG. 52 shows a cuff with overlapping, differently oriented gripping aids of loop form.

FIG. 52 shows, as an example, that the gripping aids of the invention can not only adjoin each other in the peripheral direction as well as the lengthwise direction of the cuff 2, 11 but also overlap each other. Here, four looplike gripping aids are provided on the back hand side of the cuff 2, every two loops being arranged to intersect in a cross. The individual loops are each inclined by substantially 45° relative to the lengthwise axis of the cuff 2, for example, and every two crosswise pairs of loops are positioned alongside each other at substantially the same distance from the rear edge 5 of the cuff 2, for example.

Figure 53:
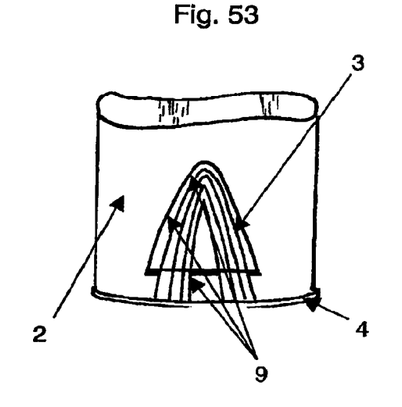
FIG. 53 shows a gripping aid variant with reinforcement fibers.

FIG. 53 shows a tongue-shaped gripping aid 3a on the back hand part of the cuff 2, pointing toward the hand part 1 of the glove, with reinforcement fibers incorporated in the gripping aid 3a itself and the connection region. This type of reinforcement of the connection or transition region of gripping aid and cuff can be provided, of course, for any configuration of gripping aid and cuff.

Figure 54:
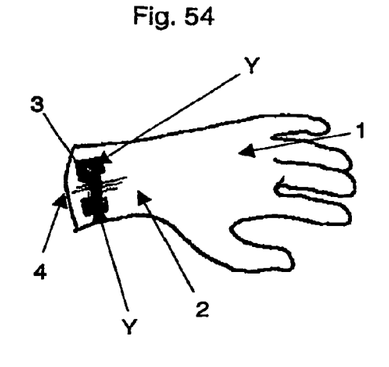
FIG. 54 shows a view of a cuff with separately fabricated looplike gripping aid mounted afterwards.

As an example for gripping aids manufactured separately and then placed on the cuff 2, FIG. 54 shows a loop-shaped gripping aid 3a for the back hand side of the cuff, which has tablike enlargements 3c at its ends facing the cuff 2, by which the gripping aid 3a can preferably be glued to the cuff 2.

Figure 55:
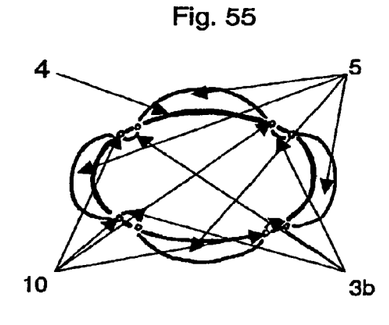
FIGS. 55 and 56 are a rear view and a top view of a glove cuff with another embodiment of a peripheral gripping aid.
Figure 56:
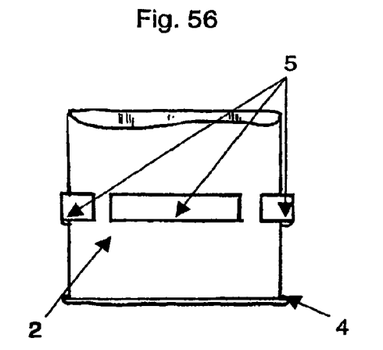

But a peripheral gripping aid can also be constructed after the embodiment shown in FIGS. 55 and 56. Here, a closed band or one with both ends fastened to the glove is passed through the cuff 2 of the glove in several places, here eight places, preferably sealed off or tightly joined to the material of the cuff at the points of passage, for example, it is glued or welded. The result is several loops (here, four) as exterior gripping aids 3, 3a on the outside of the glove, and at the same time the interior segments of the band (here again four) could be used as inner gripping aids 3b, if the points of passage through the cuff 2 are sufficiently far apart.

Figure 57:
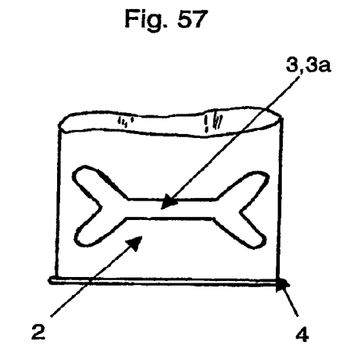
FIG. 57 shows another embodiment of a gripping aid.

FIG. 57 shows another embodiment of a gripping aid 3, 3a in which edge segments branching to the outside are joined by a straight segment lying parallel to the rear edge 4 of the cuff 2.

Figure 58:
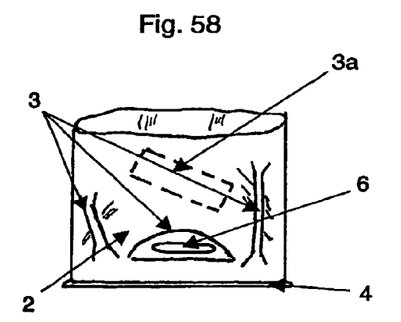
FIG. 58 is a view of a cuff with a group of adjacent gripping aids.

On the cuff 2 of FIG. 58 there is positioned a group of adjacent gripping aids 3 at a distance from each other, also for example with different orientation relative to the lengthwise axis of the cuff 2 and of different configurations, i.e., a flap-shaped gripping aid 3 with lengthwise hole 6 at the center and two loop-shaped gripping aids 3 at the sides. The dashes represent a gripping aid 3a, for example designed here as a pocket open on at least one side, which is also provided on the hand inner surface of the cuff 2.

Figure 59:
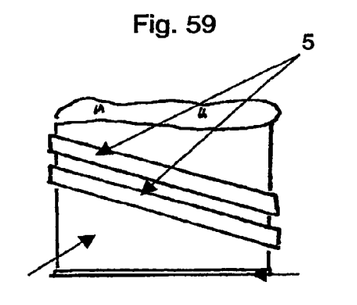
FIG. 59 shows another embodiment for peripheral gripping aids.

FIG. 59 shows as an example that peripheral gripping aids 5 can also be provided in groups. Furthermore, FIG. 59 shows as an example that these peripheral gripping aids 5 can also be oriented obliquely to the lengthwise axis of the cuff 2, and also in a different way for each of the gripping aids 5 of the group, of course.

Figure 60:
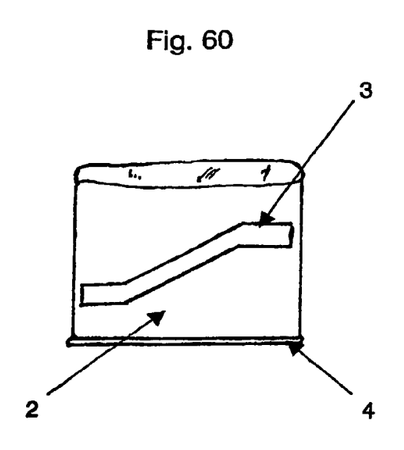
FIGS. 60 and 61 are views of gripping aids with different orientation, first merging directly into each other and then following each other with a short spacing.
Figure 61:
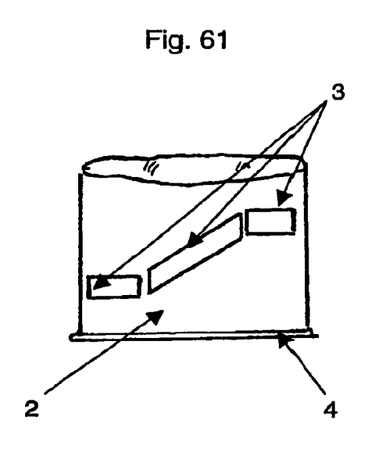

FIGS. 60 and 61 are representations of gripping aids 3 extending over a relatively large angular range from the outer wristbone region across the back hand region of the cuff 2 and changing their orientation relative to the lengthwise axis of the cuff 2 twice in their course, for example. Whereas the gripping aid 3 of FIG. 60 consists of three segments, merging directly one into another, FIG. 61 shows a group with, say, three individual gripping aids 3 of different orientation and at a short distance from each other.

The invention claimed is:
1. A method of removing a first glove from a first hand and a second glove from a second hand, which comprises:
   with the second hand, grasping at least one gripping aid positioned at a first position on a cuff of the first glove;
   with the first hand, grasping at least one gripping aid positioned at a second position on a cuff of the second glove, wherein the second position of the gripping aid of the second glove has an orientation with respect to an anatomy of the second hand that is unequal to an orientation of the first position of the gripping aid of the first glove with respect to anatomy of the first hand;

removing the first glove from the first hand by pulling the at least one gripping aid on the first glove with the second hand and simultaneously removing the second glove from the second hand by pulling the at least one gripping aid on the second glove with the first hand such that dirty or contaminated outer surfaces of the first glove and the second glove do not contact skin of the first hand or the second hand;

turning the first glove and the second glove inside-out and joining the first glove and the second glove together while performing the step of removing the first glove from the first hand and simultaneously removing the second glove from the second hand; and holding the first hand and a first arm diametrically opposite and essentially parallel to the second hand and a second arm while performing the steps of grasping and pulling the gripping aid on the first glove with the second hand and grasping and pulling the gripping aid on the second glove with the first hand.

2. The method according to claim 1, wherein the first position is near an inside of a wrist of the first hand, and the second position is near an outside of a wrist of the second hand.

3. The method according to claim 1, wherein the first position is near a thumb of the first hand, and the second position is opposite a thumb of the second hand.

4. The method according to claim 1, wherein the second position of the gripping aid of the second glove has an orientation with respect to an anatomy of the second hand that is opposite an orientation of the first position of the gripping aid of the first glove with respect to anatomy of the first hand.

5. The method according to claim 1, wherein the gripping aid on the first glove covers an outer wristbone region of a wrist of the first hand, and the gripping aid on the second glove covers an inner wristbone region of a wrist of the second hand.

6. The method according to claim 1, wherein the gripping aid on the first glove is on only one side of a peripheral section of the cuff of the first glove, and the gripping aid on the second glove is on an opposite side of a peripheral section of the cuff of the second glove.

7. The method according to claim 1, wherein the first glove and the second glove are formed from a liquid-tight elastic material.

8. The method according to claim 1, wherein the first glove and the second glove are formed from a liquid-tight elastic material, and the first glove and the second glove are formed as a work glove, an examining glove, or an operating glove.

* * * * *